United States Patent [19]
Karl et al.

[11] Patent Number: 5,674,454
[45] Date of Patent: Oct. 7, 1997

[54] STACKING DISPOSAL SYSTEM FOR TEST SAMPLE CARDS OR OTHER SIMILARLY SHAPED OBJECTS

[75] Inventors: Clifford W. Karl, St. Louis; Kent Smith, St. Charles, both of Mo.; Arthur Rousmaniere, Andover, Mass.; David Porat, Newton, Mass.; Thomas Burchard, Winchester, Mass.; Gregg Flender, Quincy, Mass.

[73] Assignee: bio Mérieux Vitek, Inc., Hazelwood, Mo.

[21] Appl. No.: 604,475

[22] Filed: Feb. 21, 1996

[51] Int. Cl.⁶ .................................................. G01N 35/10
[52] U.S. Cl. ............................... 422/63; 422/64; 422/65; 422/58; 422/104; 436/43; 436/46; 436/48; 206/456; 206/817
[58] Field of Search .......................... 422/63, 64, 65, 422/66, 67, 68.1, 104, 58; 436/43, 44, 46, 47, 48, 165; 206/456, 817; 53/447, 531, 542, 543

[56] References Cited

U.S. PATENT DOCUMENTS

| | | | |
|---|---|---|---|
| Re. 29,725 | 8/1978 | Johnson et al. | 23/230 |
| 3,963,355 | 6/1976 | Aldridge, Jr. et al. | 356/201 |
| 4,118,280 | 10/1978 | Charles et al. | |
| 4,142,863 | 3/1979 | Covington et al. | 422/63 |
| 4,265,855 | 5/1981 | Mandle et al. | 422/65 |
| 4,577,453 | 3/1986 | Hofeler | 53/438 |
| 4,766,714 | 8/1988 | Sugaya | 53/242 |
| 4,817,820 | 4/1989 | Heiland | 221/279 |
| 4,861,554 | 8/1989 | Sakuma | 422/65 |
| 5,008,082 | 4/1991 | Shaw | 422/65 |
| 5,053,198 | 10/1991 | Quenin | 422/64 |
| 5,221,005 | 6/1993 | Hayward | 206/334 |
| 5,232,665 | 8/1993 | Burkovich et al. | 422/65 |
| 5,270,006 | 12/1993 | Uchigaki et al. | 422/63 |
| 5,374,395 | 12/1994 | Robinson et al. | 422/64 |

*Primary Examiner*—Long V. Le
*Attorney, Agent, or Firm*—McDonnell Boehnen Hulbert & Berghoff

[57] ABSTRACT

A disposal system for stacking card-like objects neatly in a magazine. The cards enter the disposal system via a card entrance slot. A push plate located adjacent the slot pushes the cards past a pair of resilient snap elements in the sides of the magazine. A pressure plate is located behind the snap elements and biases the cards that have been pushed over the snap elements forward towards the rear of the snap elements. The cards are maintained in a stacked condition between the snap elements and the pressure plate. When a card is inserted into the card slot, the push plate is operated to an extended position, in which it pushes the card past the snap elements against the cards stacked between the snap elements and the pressure plate. The push plate then retracts, so as to enable another card to enter into the card slot. The user of the machine removes the magazine from the machine when the need arises or when the magazine is fully loaded with cards.

19 Claims, 14 Drawing Sheets

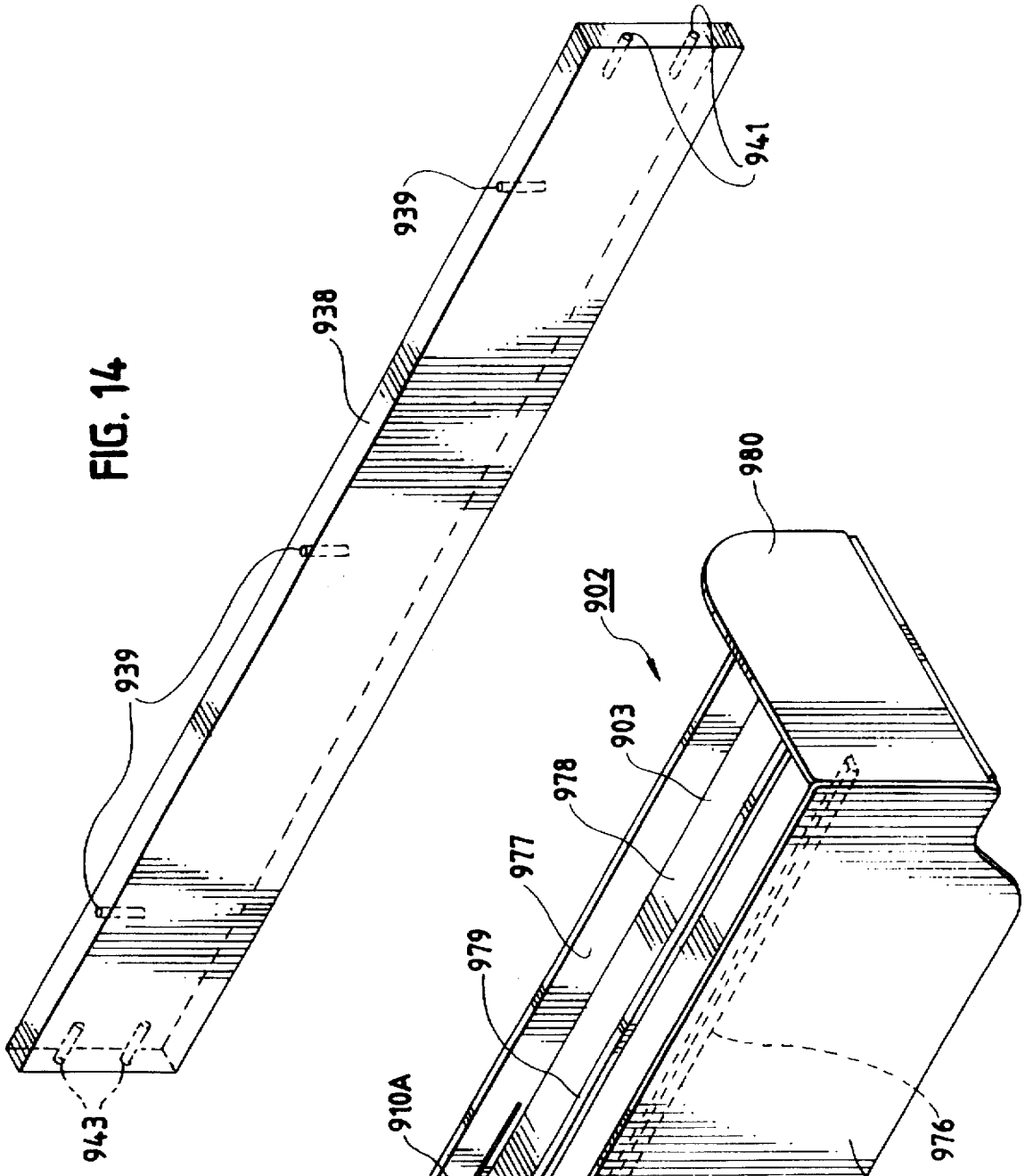

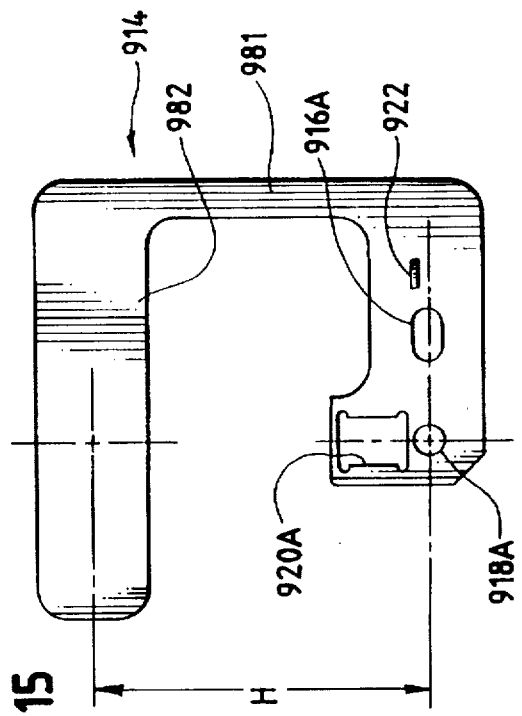
FIG. 15
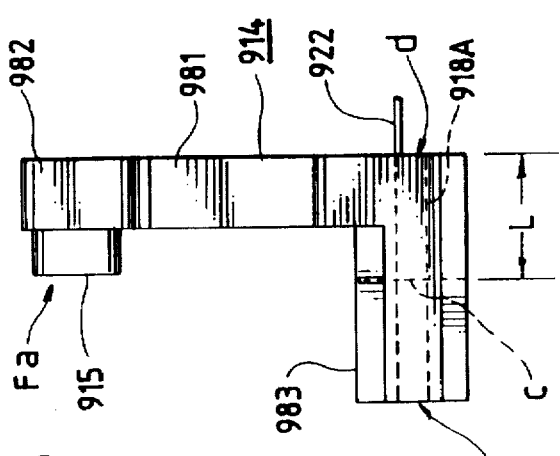
FIG. 16
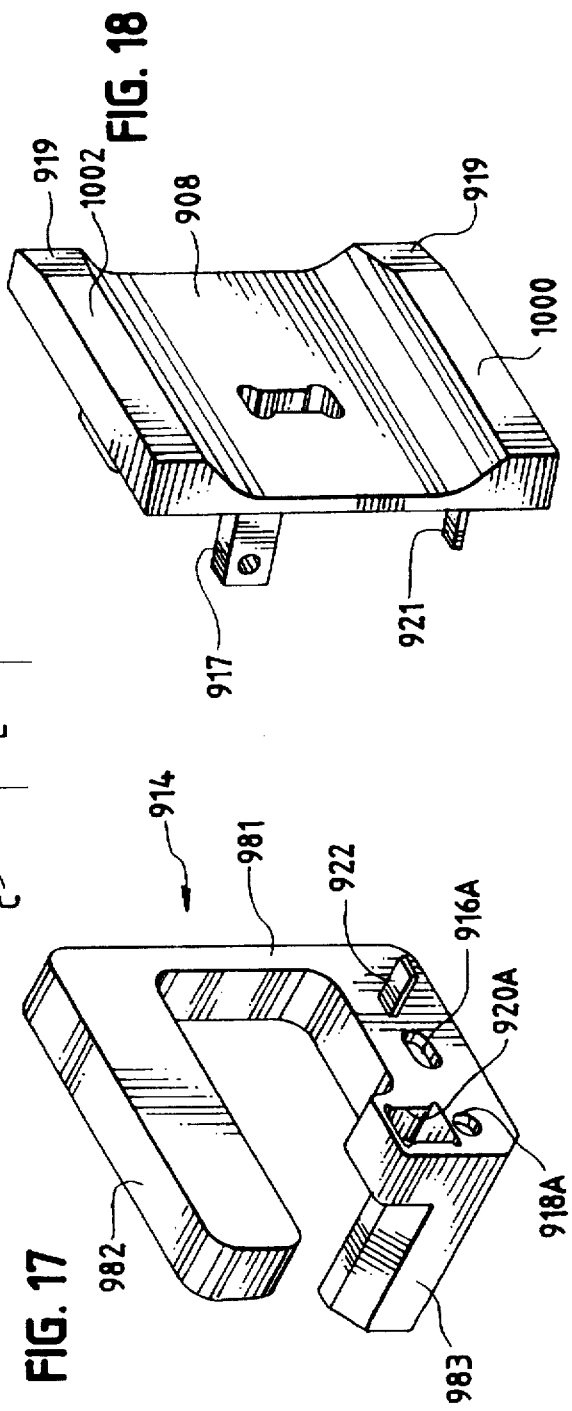
FIG. 18
FIG. 17

STACKING DISPOSAL SYSTEM FOR TEST SAMPLE CARDS OR OTHER SIMILARLY SHAPED OBJECTS

BACKGROUND OF THE INVENTION

This invention relates to the field of devices and systems for stacking cards or other similarly shaped rigid objects having flat surfaces and two parallel sides. The invention is particularly suitable for use in an automated testing machine for biological test sample cards. In such a machine, various chemical reactions occur in the cards. The cards are then read by an optical reading system and then stacked in the inventive stacking device for subsequent disposal. The stacking system is also suitable for other types of machines that require organized stacking of cards.

It is known in the art that biological samples can be stored in cards and subject to optical analysis using various techniques, including transmittance and/or fluorescence optical analysis. The purpose of the analysis may be to identify an unknown biological agent in the sample, test the sample to determine the concentration of a substance in the sample, or determine whether the biological agent is susceptible to certain antibiotics.

A technique has been developed for conducting optical analysis of biological samples that involves the use of a sealed test sample card containing a number of small sample wells. Typically, during manufacture of the cards, e.g., for microbiological analysis, the wells are filled with either various types of growth media for various biological agents, or else various concentrations of different antibiotics. The cards have a fluid port and an internal fluid passageway structure, allowing a fluid containing a biological test sample to enter the wells of the card. After the fluid samples are loaded into the card, the cards are incubated and read by an optical reading machine. An identification of unknown agents in the sample, or their susceptibility to certain drugs, can be made depending on the results of optical measurements (e.g., transmittance) of the wells.

After the card has been subject to a sufficient amount of incubation and optical analysis, it must be disposed of. One solution to the disposal of the card would be to simply dump the cards into a bag or other container. This approach has drawbacks, including cleaning and sanitization problems. Additionally, random dumping of cards makes the retrieval of a specific card from the pile of cards more difficult.

The present invention provides for an effective device that receives the sample cards once they have been subject to optical analysis, and stacks them neatly and in an organized fashion in a magazine for subsequent disposal. The magazine can be completely removed from the machine and cleaned or sterilized for reuse, if desired. The station further provides for automatic detection of when the magazine is full of cards, thus alerting the user of the need to empty the magazine. The stacking of the cards also reduces the amount of space required for the card disposal system. The inventive stacking disposal system is thus both user-friendly, efficient and sanitary.

A further advantage of the invention is that in some prior art reading systems, the cards were stored in the incubating chamber after the final reading event. The user manually removes the cards from the machine after the reading is over. If the cards are stored in the incubating station too long, the cards can "cook", potentially causing a leak in the card. The present invention achieves automatic removal of the cards from the incubation and reading stations of the machine, thereby avoiding "cooking" the cards and minimizing the chances of a leak due to too long an incubation period.

SUMMARY OF THE INVENTION

A stacking disposal system for a plurality of cards or other similarly shaped rigid objects is provided. The stacking disposal system has a magazine having a bottom surface, an end portion and first and second sides extending from the bottom surface. The magazine is removable from a machine that the stacking disposal system is mounted to. A card entrance slot is provided for receiving at least one of the cards to be stacked in the magazine. A set of snaps are located adjacent to the card entrance slot for maintaining the cards in a stacked condition in the magazine. A pressure plate having a card contact surface is provided within the magazine. The pressure plate is moveable between the snaps and the end of the magazine, with the cards being stacked in the magazine between the snaps and the pressure plate. A constant force spring is provided for biasing the pressure plate towards the snaps so as to place the card contact surface of the pressure plate in contact with the portion of one of the cards, to thereby urge the cards against the snaps and maintain the cards in a stacked condition in the magazine.

A push plate is provided on the opposite side of the card entrance slot from the snaps. The push plate has a motor that moves the push plate from a retracted position to an extended position. When the push plate is in the retracted position, a card is able to be inserted into the card entrance slot. When the push plate is moved to the extended position, the push plate pushes the card in the card entrance slot past the snaps, thereby placing the card in a stacked condition between the snaps and the pressure plate. After the card has been pushed past the snaps, the push plate returns to its retracted position, enabling another card to be placed in the card entrance slot. As this process repeats, the magazine is loaded with cards stacked between the pressure plate and the snaps.

An object of the invention is to provide a stacking disposal system for rigid card or card-like objects which automatically loads and stacks the cards in a magazine. A further object of the invention is to provide a stacking disposal system in which the user may remove the magazine from the system.

A further object of the invention is to provide a stacking disposal system which has a removable magazine, and in which the magazine has a handle feature whereby a user can remove the magazine without coming into contact with the card or other objects stacked in the disposal system.

These and other objects and features of the invention will be more apparent from the following detailed description of preferred embodiments of the invention.

BRIEF DESCRIPTION OF THE DRAWINGS

Presently preferred embodiments of the invention are depicted in the drawings, wherein like reference numerals refer to like elements in the various views, and wherein:

FIG. 13 is an isolated, perspective view of the magazine of FIG. 3;

FIG. 14 is an isolated, perspective view of the bottom vertical support of FIG. 6;

FIG. 15 is an isolated, elevated view of the pressure plate of FIG. 3;

FIG. 16 is a side view, partially in section, of the pressure plate of FIG. 15;

FIG. 17 is an perspective view of the pressure plate of FIGS. 15 and 16;

FIG. 18 is an isolated, perspective view of the push plate of FIG. 3;

DESCRIPTION OF THE PREFERRED EMBODIMENT

Overview of Preferred Sample Testing Machine

Figure 1:
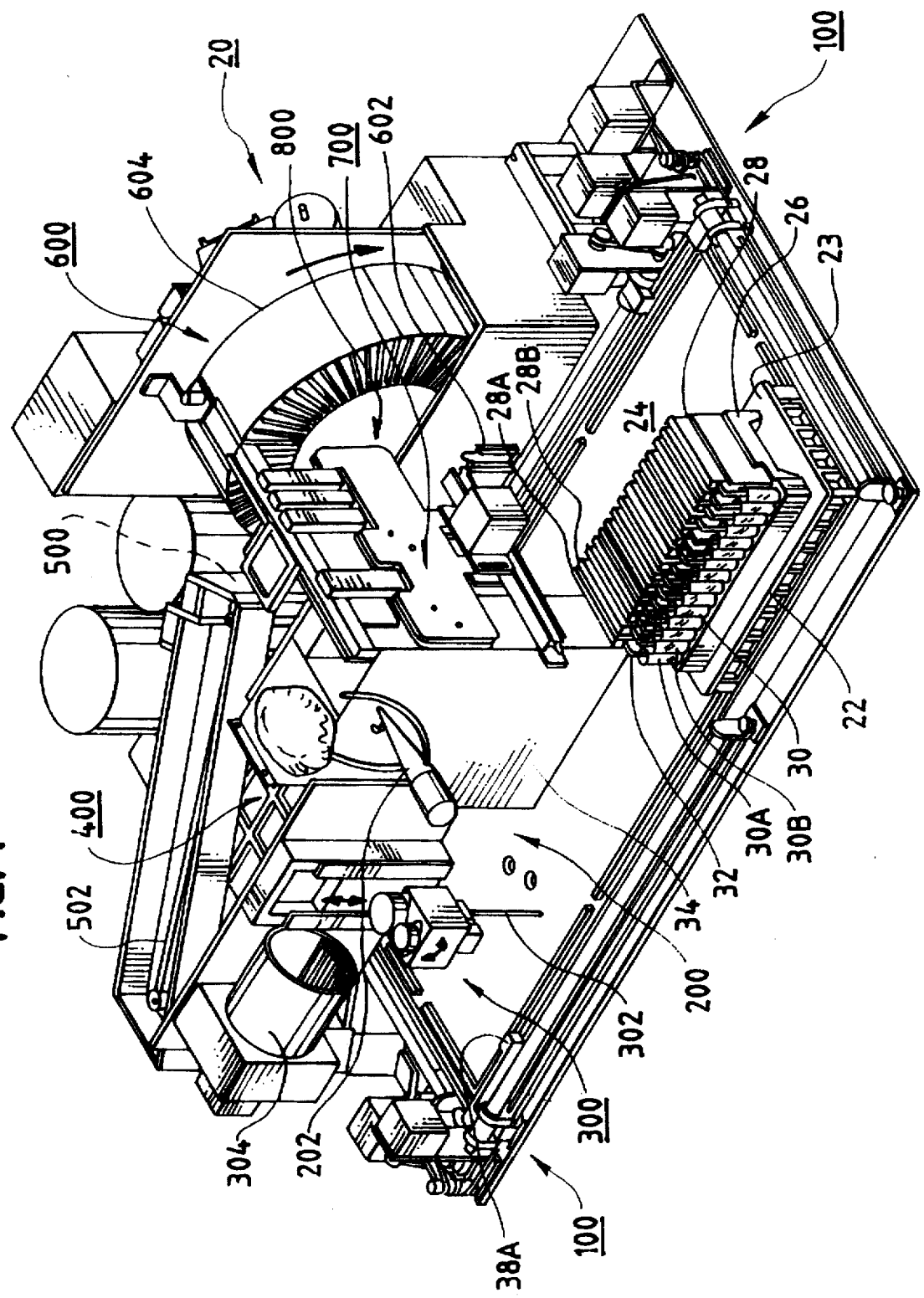
FIG. 1 is a perspective view of a preferred automatic biological sample testing machine that incorporates the stacking disposal station of the present invention, with the stacking disposal removed to better illustrate the other components of the machine.
Figure 2:
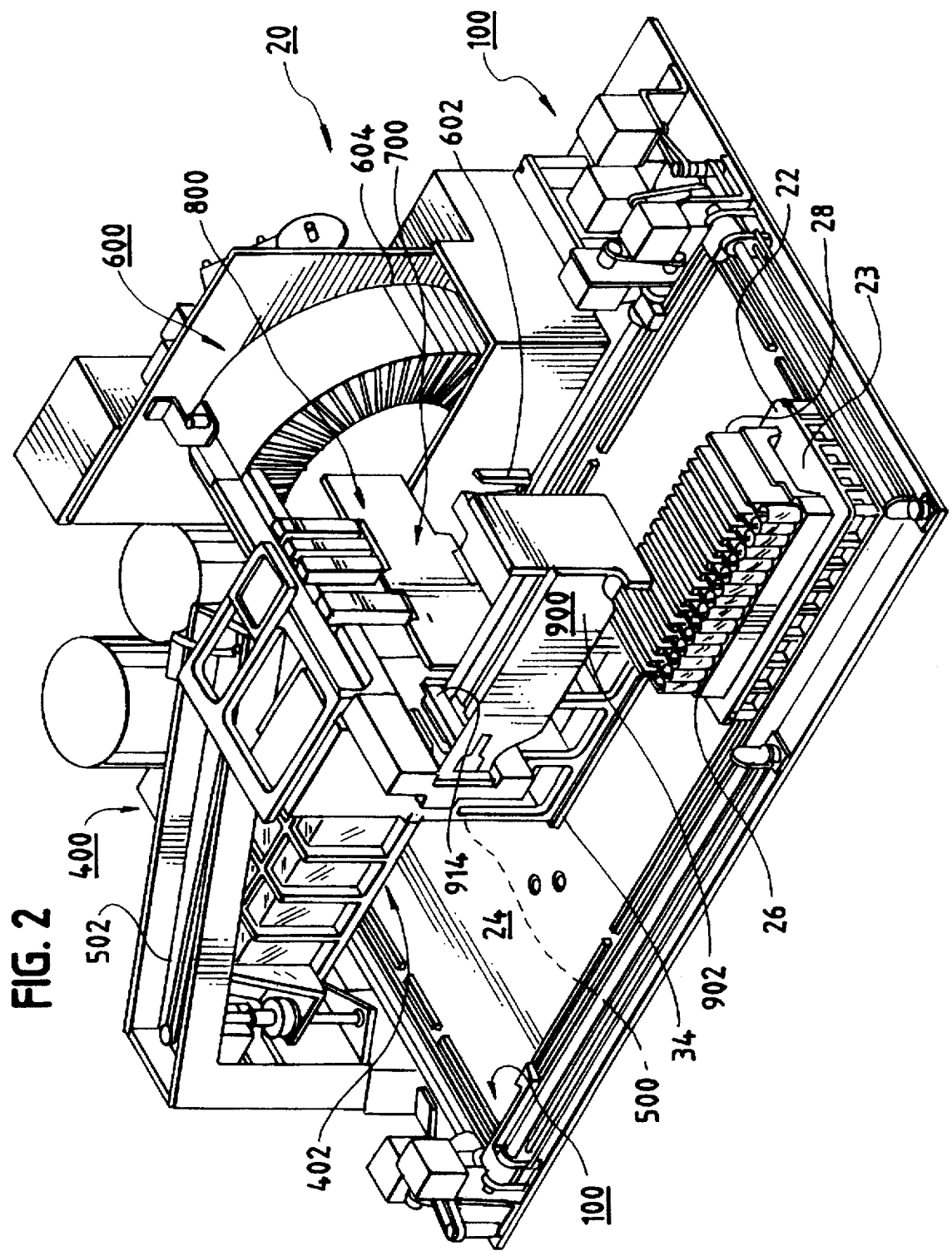
FIG. 2 is another perspective view of the machine of FIG. 1, with the stacking disposal system installed but the pipetting and diluting stations removed in order to more clearly show the vacuum chamber of the machine.

FIG. 1 is a perspective view of a preferred automatic biological sample testing machine 20 which incorporates the inventive stacking disposal system. The inventive stacking disposal system 900 is not shown in FIG. 1, in order to show the other components of the machine 20, but is shown in FIG. 2. The following detailed description of the preferred embodiment of the stacking card disposal invention will be discussed in the context of the biological sample testing machine 20. It will be appreciated, however, that the invention may be used in other types of machines having a need to stack cards or other thin card-like or similarly shaped objects, such as disc-shaped objects, which have flat surfaces and parallel sides.

The biological sample testing machine 20 includes a biological test sample positioning system 100, consisting of four independent motor-driven paddles, which is designed to slide a sample tray 22 (referred to herein as a "boat") across a base pan 24 around the machine 20 to several discrete stations, where various operations are performed on the samples in the boat 22. Prior to the start of the procedure, a technician loads a cassette 26 with a plurality of test cards 28 and receptacles such as test tubes 30 containing biological or control samples to be tested. Each test card 28 has an L-shaped transfer tube 32 protruding therefrom for permitting fluids containing the biological samples to be drawn from the test tubes 30 into the wells of the test cards 28. The technician places the loaded cassette 26 into the boat 22 at a loading station for the machine, such as the front, right hand corner of the base pan 24 shown in FIG. 1. The combined boat 22 and loaded cassette 26 are then moved as a unit over the surface of the base pan 24 about the machine 20 by the test sample positioning system 100.

In a typical microbiological testing scenario, described below for purposes of illustration but not limitation, the test cards 28 come in two varieties: (1) identification cards, in which particular different growth media are placed in the wells of the card 28 when the cards are manufactured, and (2) susceptibility cards, in which different concentrations of different antibiotics are placed in the wells of the card 28. The identification cards are used to identify the particular unknown biological agent present in the sample. The susceptibility cards are used to determine the susceptibility of the biological agent to various concentrations of antibiotics or other drugs. In the test procedure described below, identification and susceptibility tests can be performed on a single sample in one cycle of operation of the machine 20. To accomplish this, the cassette 26 is loaded such that a test tube 30A containing a biological sample, connected via a transfer tube 32 to an identification card 28A, is placed adjacent to a test tube 30B connected via a transfer tube 32 to a susceptibility card 28B. Alternate test cards may be provided for other types of biological or chemical testing, such cards incorporating various test reagents.

The cards 28 preferably contain bar codes across the top of the card for reading by a bar code reader built into the machine 20. The bar codes are unique to each card, and identify card information, such as card type, expiration date, serial number, and are used to correlate test data and/or results from the cards with the patient and the biological sample. In addition, the entire boat or cassette may have sample information for all of the cards loaded in the cassette stored on a memory device affixed to the cassette 26, such as a memory button or "touch button" available from Dallas Semiconductor Corp., 4401 S. Beltwood Parkway, Dallas Tex.

In the representative example shown in FIG. 1, seven or eight of the test tubes 30 in the boat 22 contain biological samples, and are in fluid communication with identification cards 28 by the straw-like transfer tube 32. The biological sample test tube 30A and its associated identification card 28A can be thought of as a set. The biological sample test tubes and identification cards are typically arranged in an alternating pattern in the cassette 26. Each biological sample test tube 30A and identification card 28A set is adjacent to an empty test tube 30B placed in communication with a susceptibility card 28B via a transfer tube 32. It will be appreciated that the cards and associated test tubes could be ordered in any order in the cassette 26 depending on the particular testing requirements for the samples. For example, the cards could be arranged as follows: identification (ID), susceptibility (SU), ID, ID, ID, SU, SU, ID, SU, .... Further examples would be all identification cards and all susceptibility cards.

The test sample positioning system 100 operates to move the boat 22 and cassette 26 over the base pan 24 first to a diluting station 200. The diluting station contains a rotating shot tube 202, by which a predetermined volume of diluent (such as saline solution) is added to the empty susceptibility test tubes in the cassette 26, e.g. test tube 30B. As the leading edge of the boat 22 is moved to the left during this process, it passes under a pipetting station 300. The pipetting station 300 includes a mechanism that automatically removes a pipette 302 from a source of pipettes 304, lowers the pipette 302 into the biological sample test tube 30A, and removes with vacuum a predetermined volume of biological fluid from the biological sample test tube 30A using the pipette 302.

The test sample positioning system 100 then moves the boat 22 to the left by an amount equal to the separation distance between adjacent test tubes 30A and 30B, e.g. 15 mm. The pipetting station 300 then lowers the pipette 302 containing the biological fluid from the biological sample test tube 30A into the adjacent susceptibility test tube 30B (having already received a quantity of diluent from the diluting station 200), expels the fluid into the test tube 30B, and drops the pipette 302 into the susceptibility test tube 30B. The process of movement of the boat 22 by the test sample positioning system 100, adding diluent to the susceptibility test tubes 30B at the diluting station 200, and transferring of biological samples from the biological sample test tubes 30A to the adjacent susceptibility test tubes 30B at the pipetting station 300, continues until all of the identification and/or susceptibility test tubes sets (if any) in the boat 22 have been so processed. By virtue of the close spacing of the pipetting station 300 and the diluting station 200, simultaneous diluting and pipetting operations can be performed on multiple test tubes in a single boat 22. After the last pipetting operation has been performed, the test sample positioning system 100 then moves the boat all the way to the left-hand edge of the base pan 24.

It will be understood by persons skilled in the art that the cassette 26 may be loaded entirely with biological samples in the test tubes 30 and identification cards 28, such as the case where a batch of biological samples are to be tested to identify the contents of the samples. In this example, the diluting and pipetting operations are not necessary. However, in other types of sample testing, other diluents or fluids or requests may be added to or withdrawn from the test tubes. In the example of where no diluting or pipetting operations are performed, the cassette 26 is loaded with test tubes and cards, and the positioning system 100 would simply move the boat 22 and loaded cassette 26 directly past the diluting station 200 and the pipetting station 300 without stopping, all the way to the left hand edge of the base pan 24.

Once at the left hand edge of the base pan 24, the test sample positioning system 100 operates to move the boat 22 along the left hand edge to a vacuum station 400. The vacuum station 400 is seen better in FIG. 2, which is a perspective view of the machine 22 with the diluting station 200 and the pipetting station 300 removed. At the vacuum station 400, a vacuum chamber 402 is lowered onto the boat 22 such that the bottom surface of the vacuum chamber 402 sealingly engages the top peripheral surface 23 of the boat 22. Vacuum is applied to the chamber 402 under microprocessor control, causing air in the interior of the test sample cards 28 to evacuate out of their associated test tubes and to be withdrawn from the chamber 402. The vacuum cycle is precisely managed to optimize filling using a closed loop servo system to regulate the change of vacuum and timing of the complete cycle. After a predetermined period, the chamber 402 is vented to atmosphere under microprocessor control. The venting of the cards causes the fluid in the test tubes 30 to be drawn into the cards 28, filling the wells in the cards 28.

The test sample positioning system 100 then operates to advance the boat 22 to the right across the rear of the base pan 24 to a cut and seal station 500, located behind the center mount 34 in FIGS. 1 and 2. The cut and seal station 500 consists of a hot cutting wire and attached support plate (not shown), and a drive mechanism 502 that lowers the cutting wire and support plate to the same elevation as the top portion of the transfer tubes 32 adjacent to where the transfer tubes 32 enter the test cards 28. As the boat 22 is advanced past the cut and seal station 500, the transfer tubes 32 are forced past the hot cutting wire. With the assistance of fore and aft constraints placed on the movement of the cards 28 by the walls of the cassette 26, and the lateral constraints on the movement of the card 28 by the cassette and wall structures of the machine 20, the hot cutting wire cuts the transfer tubes 32 by melting of the transfer tube material as the boat 22 is advanced past the hot cutting wire. A small stub of transfer tube material is left on the exterior of the card 28. The stub seals the interior of the card 28 from the atmosphere.

The test sample positioning system 100 then advances the boat 22 across the rear of the base pan 24 behind the center mount 34 to a carousel incubation station 600. A reciprocating cam driver is mounted to the center mount 34 opposite a slot 602 in the machine that pushes the cards off the cassette 26 one at a time through the slot 602 into a carousel 604. The carousel 604 is housed in an enclosure that is maintained at an appropriate incubation temperature of, for example, 35 degrees C. The enclosure is not fully shown in FIGS. 1 and 2 in order to show the carousel 604. The carousel 604 is rotated in synchronism with the movement of the boat 22 over the rear of the base pan 26 by the test sample positioning system 100, so as to place the next slot in the carousel 604 in line with the slot 602 opposite the next card in the cassette 26. If the carousel is only going to be partially loaded with cards, it may be adviseable to load the cards into every other slot or two periodically in order to balance out the weight distribution in the carousel 604. For example, where the carousel has 60 slots and only 30 cards are to be processed, the cards are loaded into every other slot.

After all of the cards 28 have been loaded into the slots of the carousel 604, the boat 22 is advanced along the right hand edge of the base pan 24 back to its starting position (shown in FIGS. 1 and 2) or to an exit position for removal of the cassette 26 (containing the test tubes and transfer tubes remnants) and receipt of a new cassette.

As the cards 28 are being incubated in the incubation station 600, the cards are periodically, sequentially pushed out of the slots of the carousel 604 at the top of the carousel 604, one at a time, and moved by an optical scanner transport station 700 past a fluorescence and transmittance optics station 800. The wells of the card 28 are selectively subject to transmittance and/or fluorescence optical testing by the transmittance and fluorescence optics station 800. The transmittance and fluorescence optics station 800 includes detectors and processing circuitry to generate transmittance and fluorescence data for the wells in the cards 28, and to report the data to a central processing unit for the machine 22. If the test is not complete (such as due to the test reaction not yet suitable for analsys), the transport station 700 moves the card 28 back into its slot in the carousel 604 for more incubation and additional reading.

Typically, each card will be read every 15 minutes as the carousel makes one revolution. Typical incubation times for the cards 28 are on the order of two to eighteen hours, consisting of roughly four transmittance and fluorescence data sets per hour for each of the wells in the card 28 subject to the optical analysis.

After the testing is complete, the cards are moved by the optical scanner transport system 700 into a stacking card output station 900 according to the invention shown in FIG. 2. The card output station includes a detachable magazine 902 that receives and stacks the cards 28. The magazine 902 is placed to the side of the optical station 800 at approximately the same elevation as the optical station 800. The technician removes the magazine 902 from the machine 20 as needed or when the magazine is full of cards, empties the cards into a suitable biohazard disposal unit, and replaces the magazine back into the machine 20.

Stacking Test Sample Card Disposal Station 900

Figure 3:
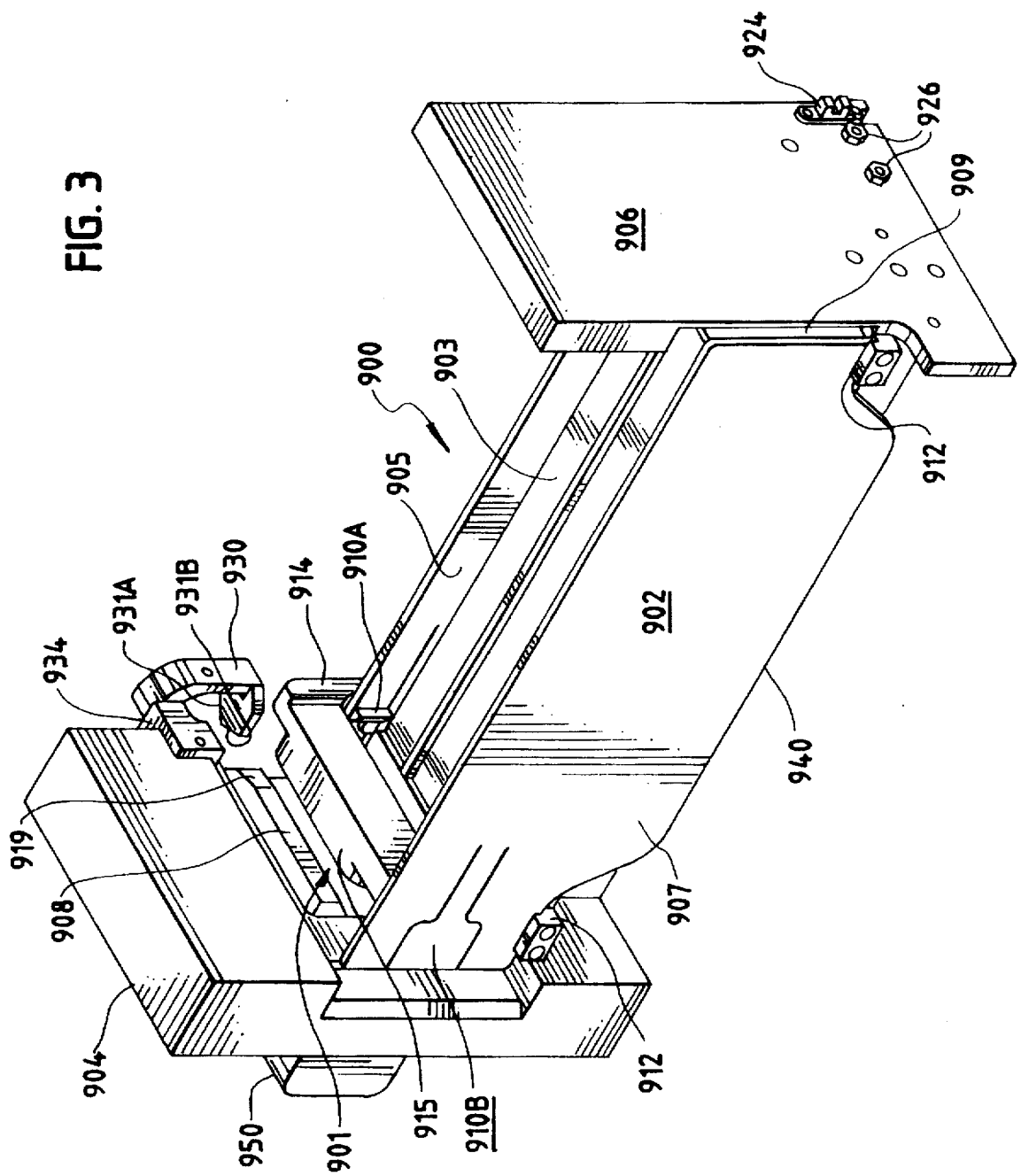
FIG. 3 is an isolated, perspective view of the stacking disposal station of FIG. 2.

Referring to FIG. 3, the stacking test sample card disposal station 900 is shown isolated from the machine 20 in a perspective view, as seen from above and in the same perspective as in FIG. 2. FIGS. 4–7 show the station 900 in various additional perspective views, both above and below the elevation of the magazine 902, in order to better illustrate the various components of the station 900.

Figure 6:
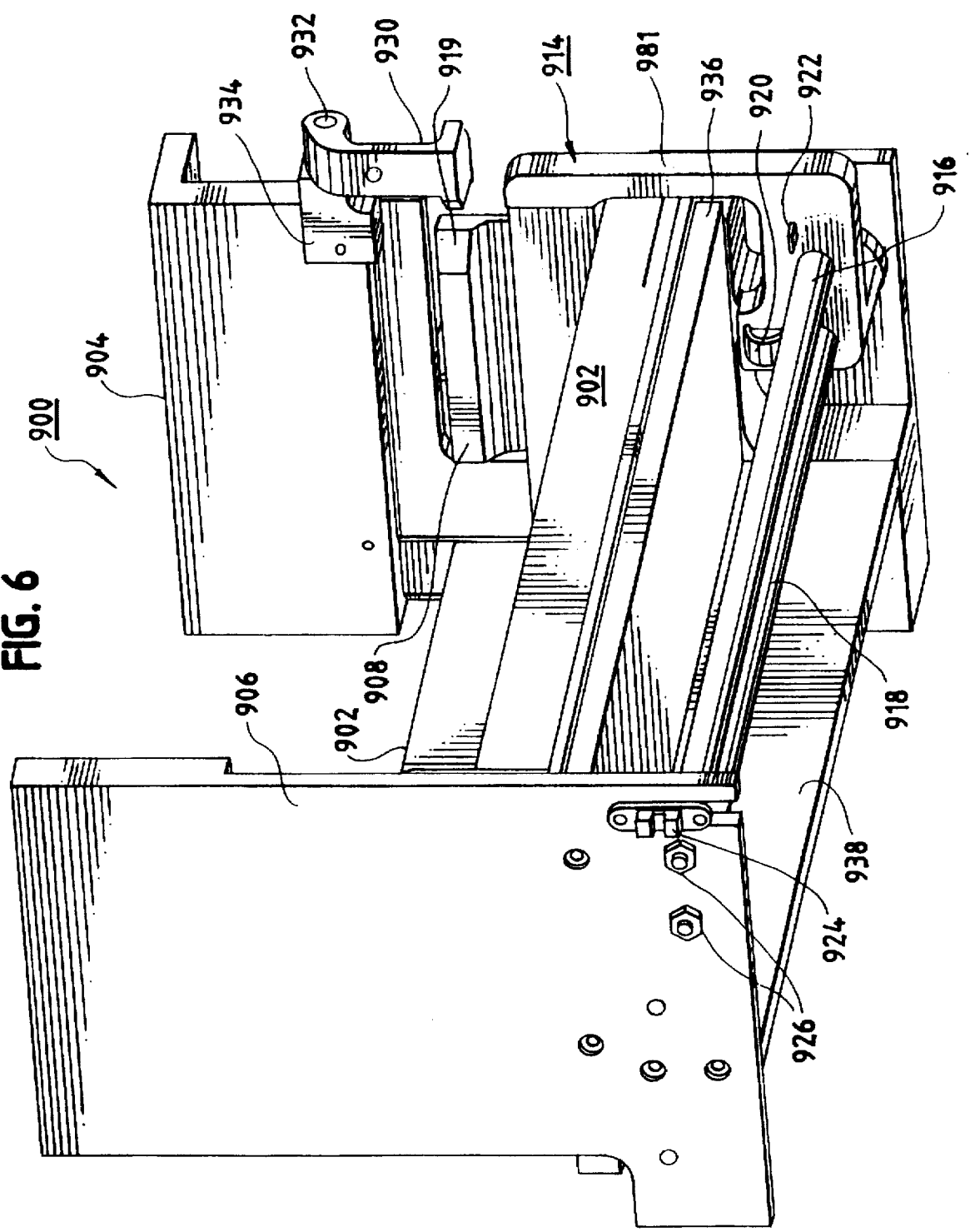
FIG. 6 is another perspective view of the stacking disposal system of FIG. 3, as seen from below and the opposite side shown in FIG. 3.
Figure 7:
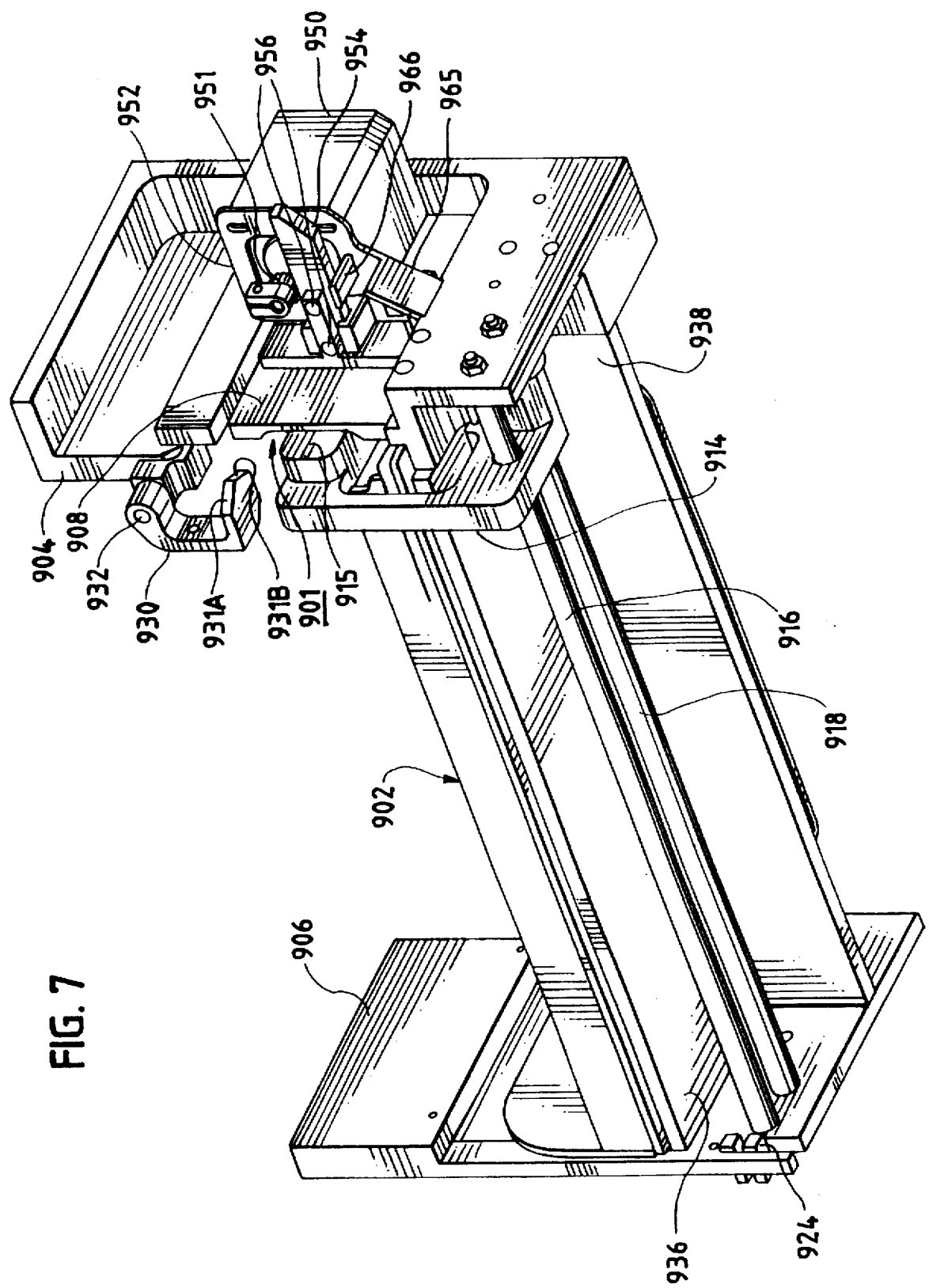
FIG. 7 is another perspective view of the stacking disposal system of FIG. 6, as seen from below and behind the left or front support plate of FIG. 3.

Referring to these figures, and in particular to FIG. 3, the station 900 has a left or front support 904, a right or rear support 906, and a removable magazine or card tray 902 which is placed between the front and rear supports 904 and 906 respectively. The magazine 902 is manually removable from the front and rear supports 904 and 906. The magazine 902 has a bottom surface 903, side portions 905 and 907 and an end portion 909 adjacent to the rear support 906. When installed in the station 900, the magazine rests on a horizontal support 936, as best seen in FIGS. 6 and 7.

When a card is ready to be stacked in the station, it enters the station 900 at a card entrance slot 901. A push plate 908 is provided opposite the front end of the magazine 902 on the other side of the card entrance slot 901. The push plate 908 is reciprocable back and forth within the card entrance slot 901 between a retracted position, shown in FIG. 3, and an extended position. When the push plate 908 is in the retracted position, a card 28 may be inserted into the slot 901 from the sample card transport station 700 (FIG. 2).

Figure 8:
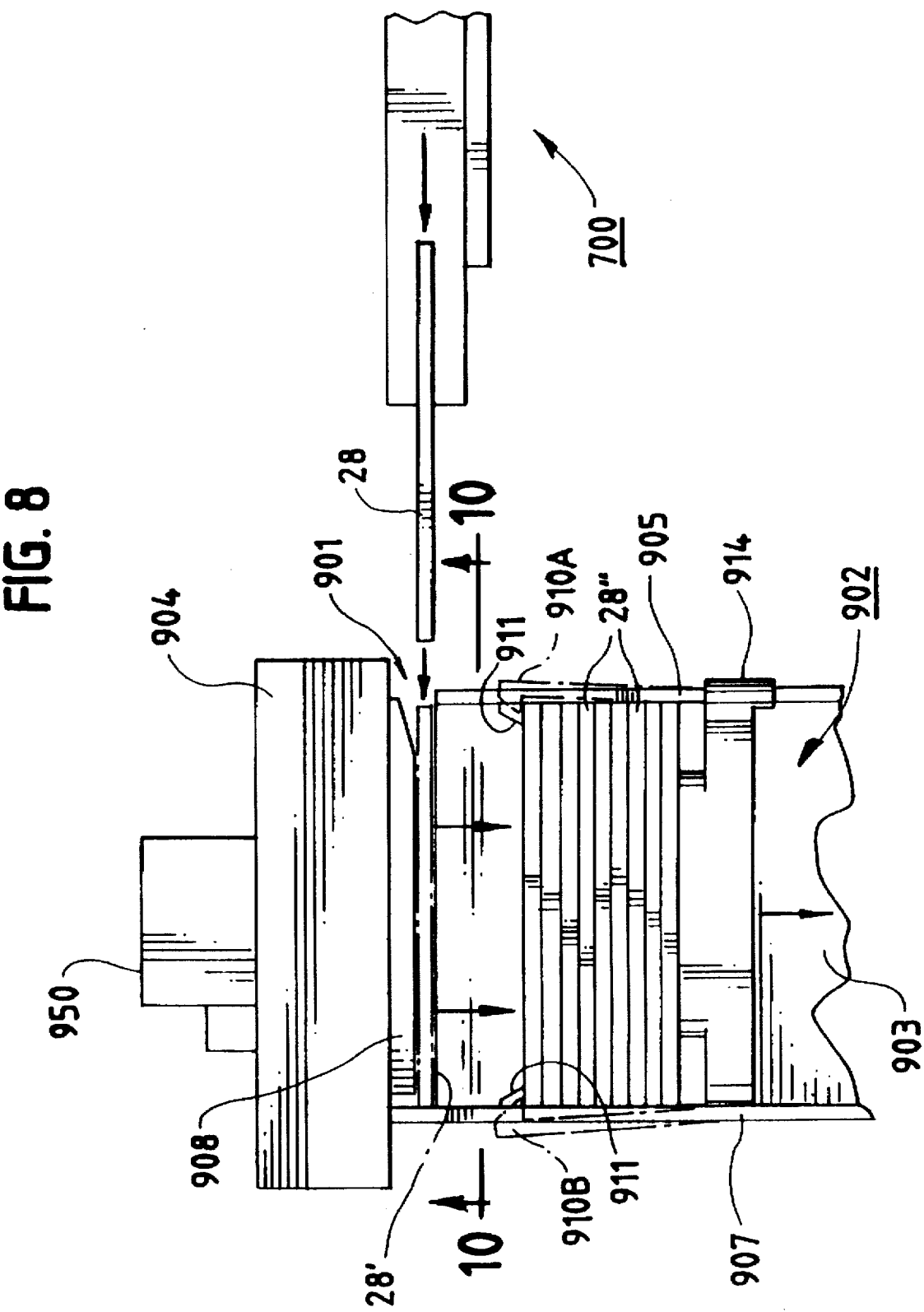
FIG. 8 is a fragmentary, top plan view of the stacking disposal system of FIGS. 3–7, showing the insertion of a card into the card slot and the push plate pushing the card over the snap elements to join the other cards stacked in the region between the rear surface of the snap elements and the pressure plate.

A pair of resilient snap elements 910A and 910B are molded into the sides 905 and 907 of the magazine 902 adjacent to the card entrance slot 901. When the push plate 908 is moved to its extended position, the card 28 in the card entrance slot 901 is pushed past the snaps 910 and stacked upright between a pressure plate 914 and the snaps 910. If there are already cards loaded in the magazine 902, the card is stacked in the stack of cards located between the snaps 910 and a pressure plate 914, as shown in FIG. 8 and described in greater detail below.

The pressure plate 914 has a card contact portion 915 that is positioned above the bottom of the magazine 902 at approximately the elevation of the middle portion of the cards. The pressure plate 914 is movable along a pair of pressure slides (or guide rails) 916 and 918 (FIG. 5), such that the pressure plate 914 is moved towards the rear 909 of the magazine 902 as additional cards are stacked in the magazine 902.

Figure 5:
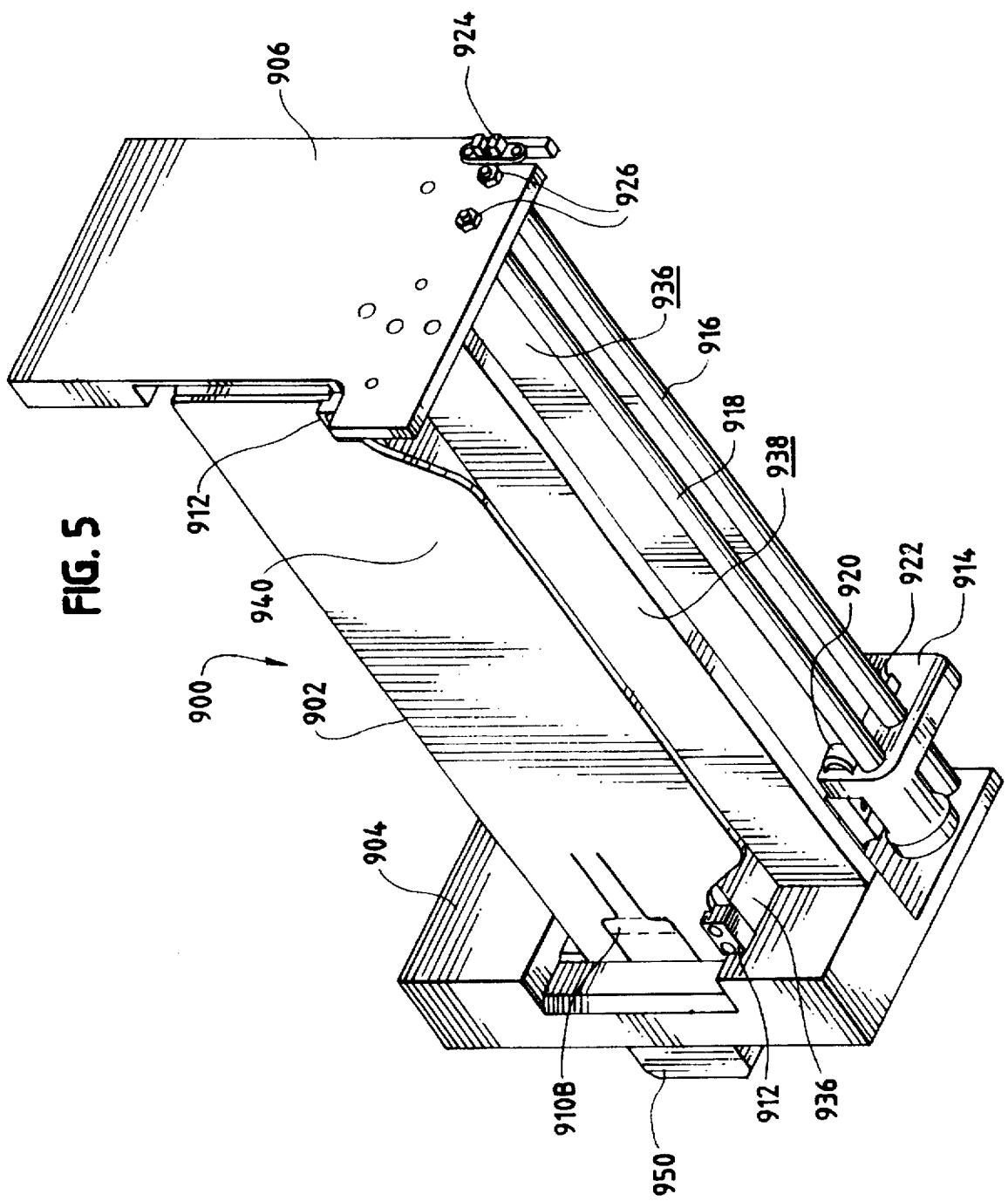
FIG. 5 is a perspective view of the stacking disposal station of FIGS. 3 and 4, as seen from below, showing the pair of guide rails along which the pressure plate is slid.
Figure 11:
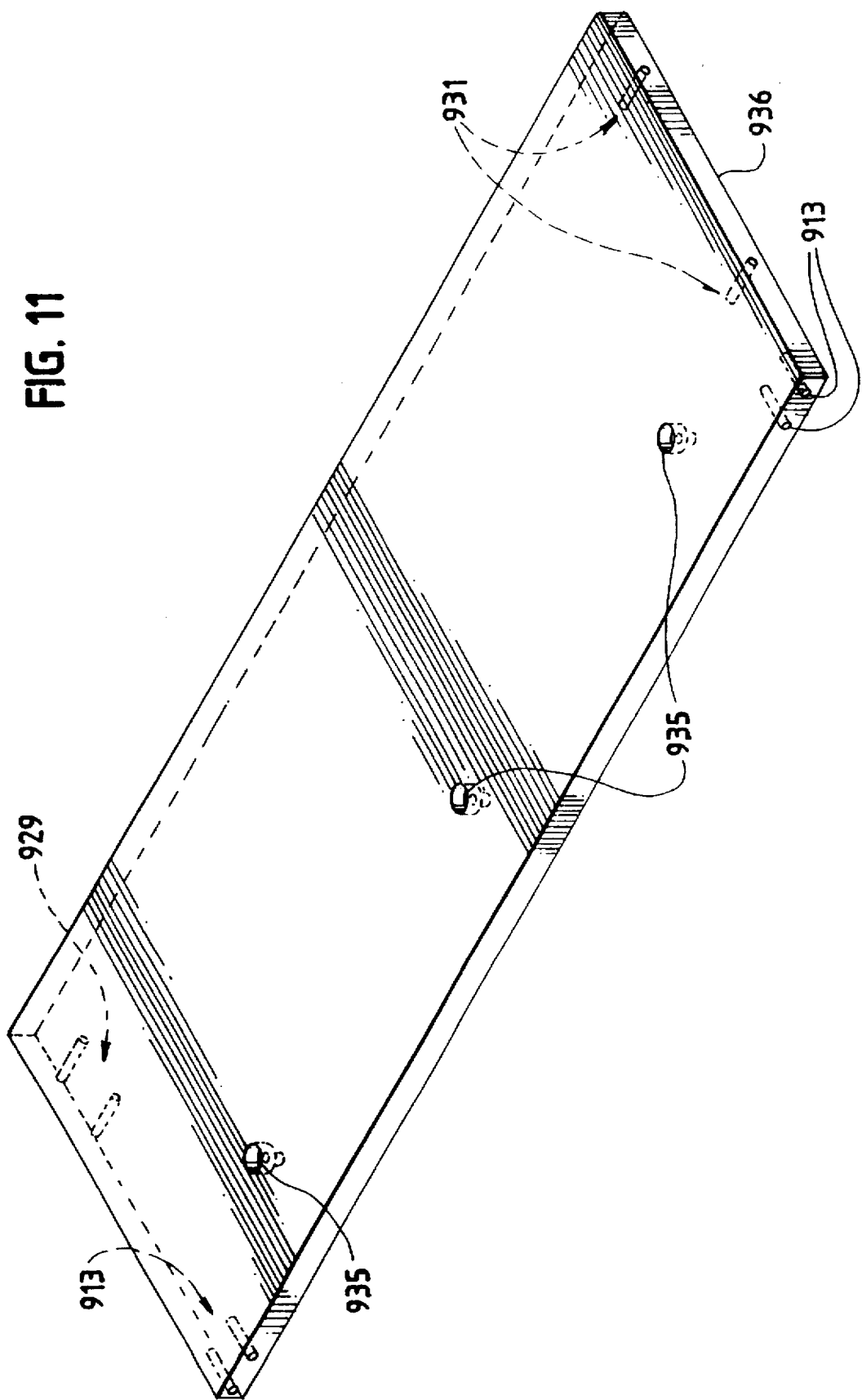
FIG. 11 is an isolated, perspective view of the horizontal support of FIG. 6.

A pair of magazine retainers 912 are mounted to a horizontal support member 936 (FIGS. 5, 7, 11). When the magazine 902 is mounted to the station 900 as shown in FIG. 3, the retainers 912 securely maintain the magazine 902 between the front and rear supports 904 and 906. The magazine 902 has a handle portion 940 in the side 907 which allows the user to grasp the magazine 902 and slide it over the retainers 912 to thereby lift the magazine 902 out of the station 900 for disposal of the cards stacked in the magazine 902. The handle 940 is located at the lowermost portion of the magazine side 907 so as to prevent accidental contact with one of the cards 28 during the magazine removal operation.

Referring to the fight hand side of FIG. 3, a pair of nuts 926 are provided to secure the pressure slides 916 and 918 against the rear support 906. An optical sensor 924 is mounted to the rear support 906, adjacent to and below the end 909 of the tray 902. The sensor 924 detects when the pressure plate 914 is positioned all the way at the rear of the magazine 902, indicating a full magazine 902.

Referring now to the left-hand side of FIG. 3, a stepper motor 950 is mounted behind the front support 904. The motor 950 moves the push plate 908 back and forth between the extended and a retracted positions relative to the card entrance 901. The push plate 908 has an angled card slide surface 919 which facilitates the insertion of the card into the slot 901. A latch 930 is mounted by a bracket 934 to the front support 904. The latch 930 has a card slide surface 931A which assists the card to easily enter the card entrance slot 901, causing the latch 930 to pivot about the pivot pin 932 (FIG. 7). The weight of the latch 930 causes a second card contact surface 931B to push the card 28 into the slot 901, using a wedging effect to ensure that the card 28 is free of the test card transport station 700 and is all the way into the stacking disposal station 900.

Figure 4:
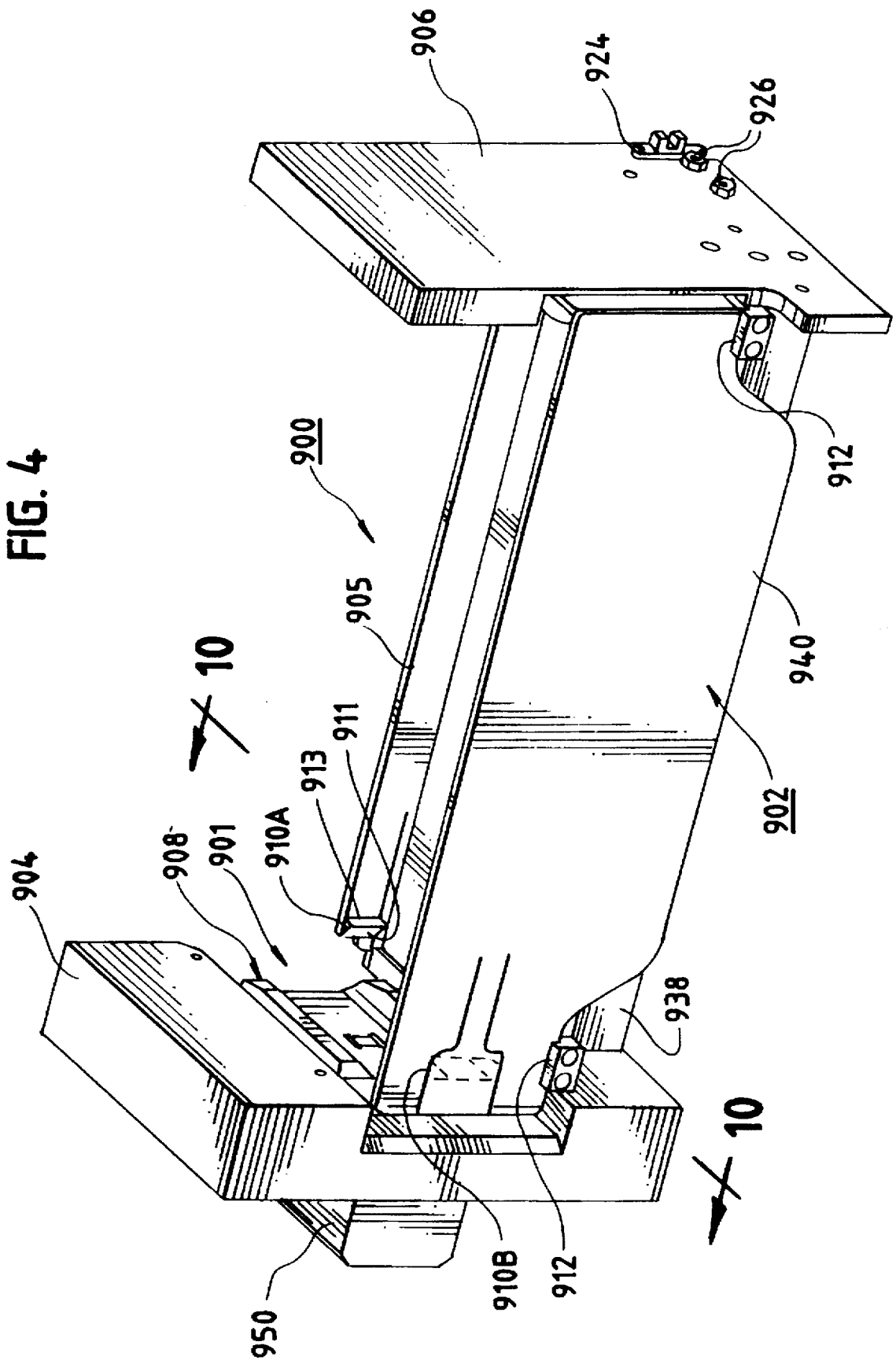
FIG. 4 is another perspective view of the stacking disposal station of FIG. 3, with the latch and pressure plate removed in order to better illustrate the card slot and snap element 910A.

Referring now to FIG. 4, the stacking disposal station 900 is illustrated in a perspective view with the pressure plate 914 and latch 930 of FIG. 3 removed. The snap 910A has a slanted surface 911 and a rear surface 913. When the push plate 908 pushes the card against the snap 910A, the card engages the slanted surface 911 and forces the resilient snap 910A to flex outwardly such that the card is pushed past the snap element 910A, at which point the resilient snap 910A returns back into the position shown in FIG. 4. In this position, the card is pushed against the rear surface 913 of the snap 910A by the pressure plate 914 (FIG. 3). The structure and operation of the snap element 910B is the same as that just described for the snap element 910A.

Referring now to FIG. 5, the stacking disposal station 900 is shown in a perspective view slightly below and towards the support 906 of the station 900. The tray retainers 912 are mounted to the horizontal support member 936 which supports the magazine 902. The horizontal support member 936 is mounted to the front and rear support members 904 and 906 respectively by screws or other suitable fastening devices. A vertical reinforcing support member 938 is provided to support the mass of the horizontal support member 936 and the magazine 902.

The pressure plate 914 is mounted to the device 900 by a pair of pressure slides 916 and 918 which extend transversely underneath the magazine 902. The pressure slides 916 and 918 are received by complimentary apertures in the pressure plate 914. A constant force spring 920 comprising a metal coil is provided with a first end fixed relative to the left support 904 and a second end which is received in a pocket in the pressure slide 914. As the magazine 902 is loaded with cards one by one, the pressure plate 914 is moved stepwise towards the right towards the rear 909 of the tray 902. However, the constant force spring 920 continually biases the pressure plate 914 forward towards the snaps 910 with a force independent of the position of the pressure plate 914 within the magazine 902 (and thus independent of the number of cards loaded in the magazine).

Referring now to FIG. 6, the station 900 is shown again from below and slightly to the side of the station 900, on the opposite side shown in FIG. 3. The pressure plate 914 has a flag element 922 extending outwardly from its rear surface. When the magazine 902 is fully loaded, the pressure plate 914 has been moved to end of the magazine 902, and the presence of the flag 922 adjacent to the rear support 906 is detected by an optical detector 924. As best shown in FIG. 7, the optical detector 924 is placed in the rear support 906.

Referring to FIG. 7, the pressure plate 914 has a card contact surface 915 which pushes against the central portion of the card inserted into the card slot 901. FIG. 7 also shows the drive assembly for the push plate 908. The push plate stepper motor 950 is mounted to a push slide bracket 952. The motor 950 has a pinion gear 951 having a set of teeth that engage complimentary teeth on the upper edge of a push rack 954. The push rack 954 is mounted to the rear of the push plate 908 via screws 956 and slides back and forth on the push slide 952. The operation of the motor 950, pinion gear 951 and push rack 954 causes the push plate 908 to move back and forth in the card entrance slot 901 between a retracted position shown in FIG. 7 and an extended position, in which the push plate 908 pushes a card past the resilient snap elements 910A and 910B.

FIG. 8 is a top plan view of the front portion of the magazine 902, illustrating the stacking operation in greater detail. When the test sample card 28 is loaded into the card slot 901, it is located in a position 28' shown in dashed lines in FIG. 8. The motor 950 causes the push plate 908 to move to its extended position, pushing the card 28 against the slanted surface 911 of the resilient snap elements 910A and 910B. This causes the snaps 910 to flex outwardly, as shown in dashed lines, pushing and stacking the card 28 against the other cards 28" that had been positioned between the snap elements 910 and the pressure plate 914. The force of the motor 950 pushes the pressure plate 914 towards the rear of the magazine 902. After the card 28 has been loaded into the magazine 902, the motor 950 operates to retract the push plate 908 thereby permitting another card 28 to be loaded into the card slot 901.

Figure 9:
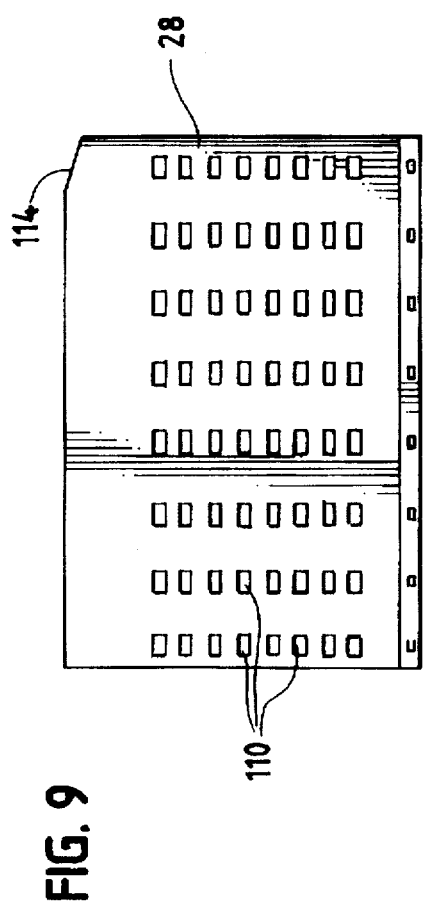
FIG. 9 is a plan view of a preferred test sample card for use with the stacking disposal system.
Figure 10:
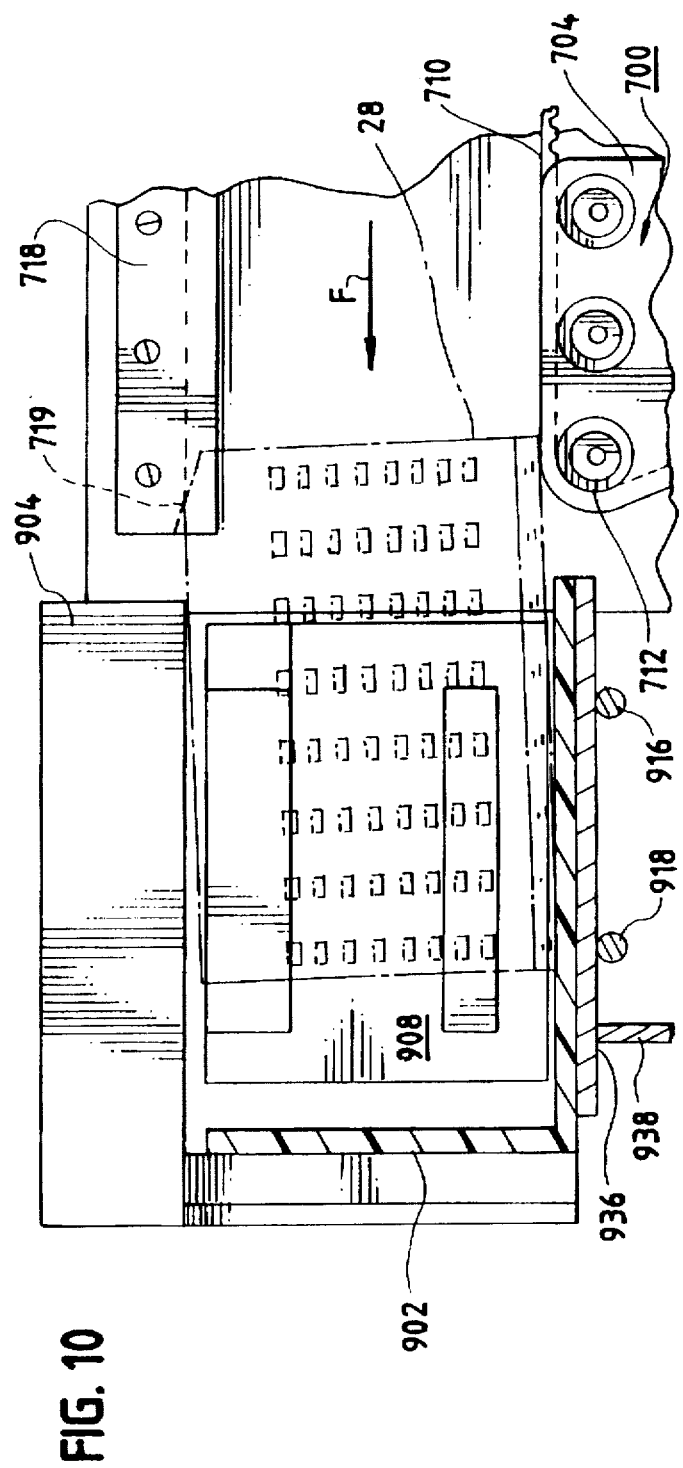
FIG. 10 is an elevational view, partially in section, showing the loading of the cards into the card slot by the sample card transport system of FIG. 1.

The card 28 for the illustrated embodiment is shown in a plan view in FIG. 9. The card 28 has a plurality of sample wells 110 which are subject to the optical analysis in the reading station 800. A slanted shoulder 114 is provided on the upper edge of the card 28. The loading of the card 28 into the card entrance slot 901 is shown in FIG. 10, which is a sectional view of the station 900 along the lines 10—10 of FIG. 8. The sample card transport station 700 has a stepper motor (not shown) that drives a drive belt 710 along a series of rollers 712 mounted to a cover plate 704. The card 28 is snugly positioned between the drive belt 710 and a ledge 718 mounted to a bulkhead. The ledge 719 has an internal card slot that receives the top edge of the card 28. The card slot has a slant portion 719 at the extreme left-hand end of the ledge 718. When the card 28 is moved past the end of the cover plate 704 onto the tray 902, the slanted shoulder 114 of the card 28 is placed into contact with the slant portion 719. The tray 902 is slightly lower than the elevation of the belt 710 at the top of the cover plate 704, assisting the placement of the upper shoulder 114 against the slant 719. A resultant pinching force F (FIG. 10) is imparted to the card 28 by the drive belt 710 and slant portion 719 in the direction of the magazine 902, causing the card 28 to snap out of the drive assembly 700 into the slot 901.

Figure 12:
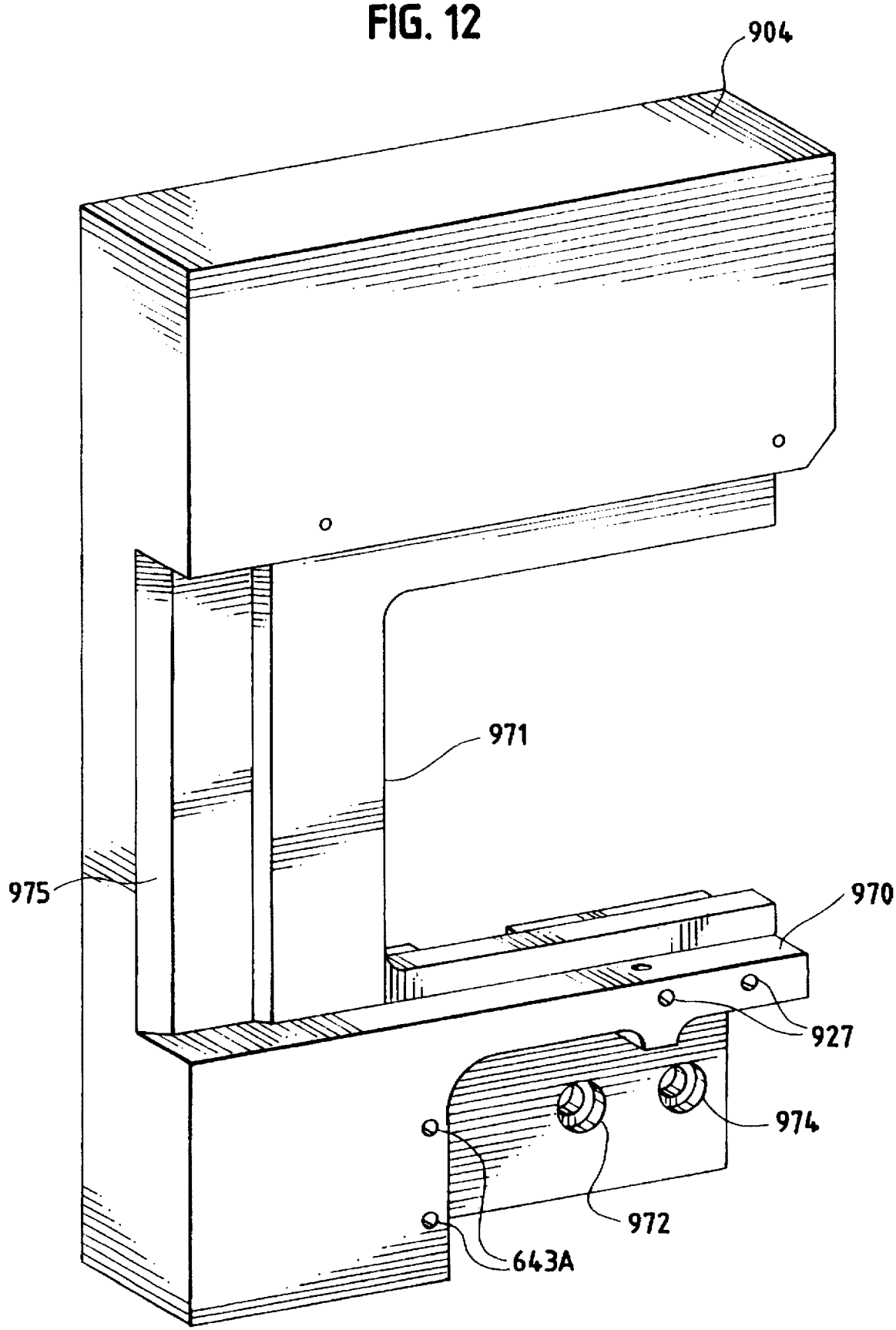
FIG. 12 is an isolated, perspective view of the front support of FIG. 3.

Referring now to FIG. 12, the left or front support 904 of FIG. 3 is shown isolated in a perspective view. The left support 904 includes a pair of through holes 972 and 974 which receive the guides 918 and 916 for the pressure plate 914. A pair of mounting holes 943A are provided for the vertical support member 938 shown in FIGS. 5 and 14. A pair of mounting holes 927 are provided to secure the horizontal support member 936. The support 904 has a ledge 970 which supports the far left hand edge of the magazine 902. The tapered portions 975 on the side of the support 904 assist in the easy insertion of the magazine 902 into the station 900. The support 904 has a wall portion 971 which defines an opening for the push plate 908.

The magazine 902 is shown isolated in a perspective view in FIG. 13. The location of the large snap 910B on the left hand side 907 of the magazine 902 is set so it does not interfere with the stub of the transfer tube 32 that may be present on the exterior surface of the card 28. The snap elements 910A and 910B are designed so that they are a molded part of the magazine sides. The bottom surface 903 of the magazine 902 has a pair of raised ridge elements 976, 979 which support the card 28 slightly above the bottom surface 903 of the magazine 902. The magazine is designed to hold a small amount of fluid if a card were to leak.

Preferably, the magazine 902 is made out of polycarbonate. This material can withstand high temperatures, can be occasionally autoclaved, and has excellent flexural properties for the snap elements 910A and 910B. Polycarbonate can be deformed without cracking. Therefore it is not likely that a snap 910A and 910B will break as the cards are pushed over the snaps.

Referring now to FIG. 14, the vertical support 938 is shown isolated. The support 938 has a pair of holes 943 that receive mounting screws for mounting the support 938 to the left support 904. The holes 941 are provided for mounting the support 908 to the rear support 906. The holes 939 are for fastening the support 938 to the horizontal support 936. The horizontal support is shown isolated in FIG. 11, and includes a set of three recesses 935 for a fastener attaching the vertical support 938 to the horizontal support 936. The horizontal support has a set of holes 929 that receive screws for mounting the horizontal support 936 to the left or front support 904, and a set of holes 931 for mounting the support 936 to the rear support 936. The holes 913 receives the screws for the magazine retainers 912 of FIG. 3.

Referring now to FIGS. 6 and 17, the constant force spring 920 is installed in the pocket 920A in the pressure plate 914, thus eliminating an axle for the spring 920. The spring 920 is located such that it helps prevent binding of the pressure plate 914 by providing a moment in the opposite direction of the moment caused by a card pressing against the card contact surface 915 of the pressure plate 914. A hole 916A in the pressure plate 914 for the guide 916 is provided so that the parallel alignment of the two guide rails 916 and 918 is not critical. The slides 916 and 918 are positioned under the assembly 900 so that they are away from the user.

Referring to FIGS. 15 through 17, the pressure plate 914 has a card contact arm 982 having a card contact surface 915, a slide collar 983 receiving the pressure slide guide rail 918 in the aperture 918A, and an integral body portion 981 connecting the slide collar 983 to the card contact arm 982. When the pressure plate 914 is installed, the card contact portion 982 is located above the bottom portion of the tray 902, with the body portion 981 extending on the outside of the magazine 902 adjacent to the side portion 905. When the magazine 902 is inserted in the station 900, the side 905 of the magazine 902 slips underneath the card contact arm 982.

A force analysis of the slide and pressure plate assembly of the FIGS. 5 and 16 dictates that, for the pressure plate 914 to move towards the rear of the tray 902 and not bind, the force imparted by the push plate 908 onto the card contact surface 915, Fa, must be greater than the frictional forces applied to the pressure plate 914 at points d and e. The frictional forces at d and e are supplied by the moment created around point C, the center of the collar 983. The length L of the surface within the collar portion 983 that bears on the slide rod 918 is chosen to be sufficiently long such that the frictional force between the collar portion 983 and the slides 916 is always less than the force applied by the push plate 908 onto the cards 28. This prevents binding of the pressure plate 914. The clearance fit between the pressure plate 914 and pressure slides 916 and 918 is an ANSI preferred hole basis metric clearance fit, no. H8/f7. In a preferred embodiment, with the pressure plate 914 material chosen to be White Acetron GP having a coefficient of friction of 0.25, and a height H between the center of the aperture 918A and the center of the card contact surface 915 being 59 mm, the length L must be greater than 14.75 mm, and preferably is 21.4 mm. The ratio of the collar 983 length (distance from d to e) to the distance H between the slide rail and card contact arm is chosen such that the force of friction between the collar 983 and rail 918 will always be less than the force applied by the push plate 908, thereby preventing the pressure plate 914 from binding.

The guides 916 and 917 are preferably stainless steel shafts to prevent corrosion, because parts of the assembly may be chemically contaminated. Preferably, the pressure plate 914 is selected of a light color material so that it will show dirt.

The push plate 908 is shown isolated in a perspective view in FIG. 18. The push plate is provided with upper and lower card contact surfaces 913 and 915 which contact the top and bottom portions of the card 28. The push plate 908 is made from a light-colored dimensionally stable plastic with a coefficient of friction, such as White Acetron GP. The upper and lower slanted surfaces 919 facilitate the easy insertion of a card 28 into the card slot 901 shown in FIG. 3. Extending outwardly from the back side of the push plate 908, a horizontally extending securing member 917 is provided for mounting the push plate from the push rack 954, as shown in FIG. 7. Preferably, the push rack 954 is also made from White Acetron GP.

Figure 20:
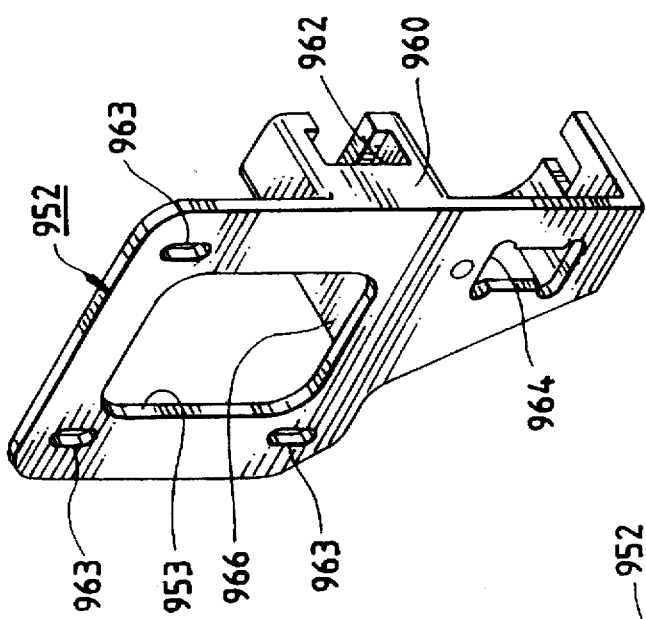
FIG. 20 is a perspective view of the push slide from the push plate drive assembly of FIG. 7.
Figure 22:
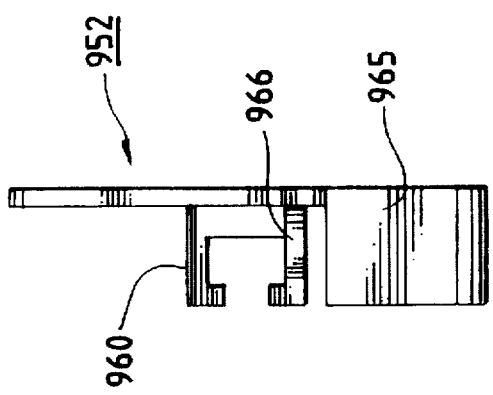
FIG. 22 is a side view of the push slide of FIG. 21.
Figure 21:
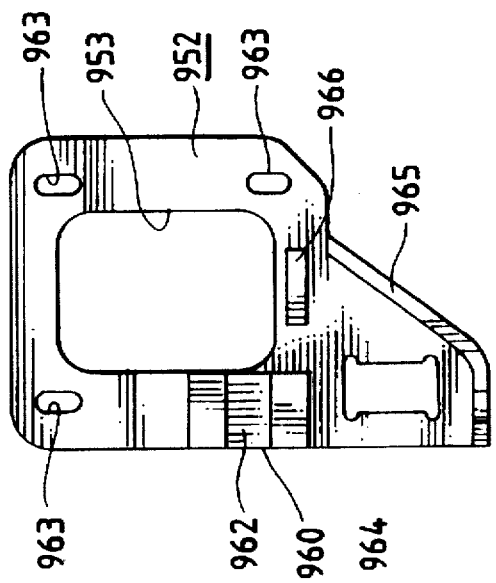
FIG. 21 is a front elevational view of the push slide of FIG. 20.

Referring to FIGS. 7 and 20, the push slide 952 has a central opening 953 which receives the push plate motor 950. A set of 3 slotted motor mount holes 963 are provided in the push slide 952. The slotted mounting holes 963 allow adjustments to the motor 950 position so that the gear 951 of the motor 950 will not make noise. The push slide 952 also contains an optical sensor mounting aperture 964 which receives an optical sensor (not shown) to detect when the push plate 908 is in a retracted position. The push slide 952 also has a C-shaped push rack slide 960 which defines an opening 962 receiving the push rack 954. A horizontal support surface 966 is provided to support the aft end of the push rack 954 as it is slid back and forth by the motor 950 within the C-shaped slide 960. The push slide 952 is shown in an elevational view in FIG. 21. The push slide 952 is shown in a side view in FIG. 22. Referring to FIG. 18, a flag element 921 extends horizontally from the rear surface of the push plate 908. When the push plate is in its retracted position, the flag element 921 is detected by the optical sensor installed in the aperture 964 of the push slide 952.

Figure 19:
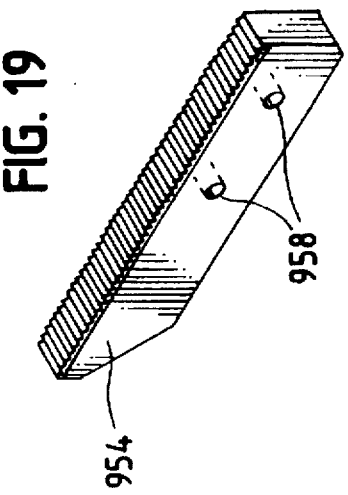
FIG. 19 is a perspective view of the push rack of the push plate drive assembly of FIG. 7.

Referring to FIG. 19, the push rack 954 has a set of teeth which are engaged by the pinion gear 901 of the motor 950. A set of mounting holes 958 are provided to secure the push rack 954 to the mounting member 917 on the push plate 908 (FIG. 18).

In the preferred embodiment, the firmware code of the station 900 is designed to count the number of steps that the stepper motor 950 takes to move the push plate 908 from its retracted positions to its extended position, and count the number of steps to retract the push plate 908 back to its retracted position. This counting process serves the function of detecting an obstruction in the card slot. For example, the firmware code may count 140 steps to move the push plate 908 to its extended position. When the push plate 908 is retracted to its retracted position, the program counts the number of steps to move the push plate 908 back until the sensor detects the flag 919 on the rear of the push plate 908. The code then compares the number of steps out to the number of steps in. If they do not match, the cycle is repeated, with the assumption that there must be a jam if the number of steps do not match. If the number of steps do not match after ten cycles then the procedure is aborted and the user notified of the jammed condition. Preferably, the gear size for the motor 950 is selected to maximize the motor speed while minimizing the push plate speed, thereby providing a relatively high number of counts. The electronics that controls the motor 950 uses a chopper driver to provide the necessary torque.

It will be apparent from the above description of a preferred embodiment of the invention that some modification and variation can be made to the preferred embodiments to suit the particular dimensions or shapes of the cards, without departure from the spirit and scope of the invention. For example, if the cards were circular discs, the bottom of the magazine 902 would have to be shaped in a manner to accommodate the discs, and different type of drive mechanism might be required to load the discs into the magazine 902. However, the basic principles of operation of the stacking disposal system would remain unchanged. The choice of materials and components is dictated by the application for the stacking system and the dimensions of the cards.

Further, while the presently preferred embodiment of the invention has been described in conjunction with a biological sample test card as the object being stacked, the invention is applicable to other types of machines besides sample testing machines in which rigid card-like objects having flat surfaces and parallel sides are to be stacked. This true spirit and scope of the invention is defined by the appended claims, as interpreted in light of the forgoing.

We claim:

1. A stacking disposal system for a plurality of cards having a flat surface and parallel sides, comprising:
- a magazine having a bottom surface, an end portion and first and second sides extending from said bottom surface;
- a card entrance slot for receiving at least one of said cards to be stacked in said magazine;
- resilient snap means located adjacent to said card entrance slot for retaining said cards in a stacked condition in said magazine;

a pressure plate moveable within said magazine between said snap means and said end portion of said magazine, said cards being stacked in said magazine between said snap means and said pressure plate, said pressure plate having a card contact surface;

means for biasing said pressure plate towards said snap means so as to place said card contact surface of said pressure plate in contact with a portion of one of said cards to thereby urge said cards against said snap means; and push plate means, reciprocable relative to said card entrance slot from a retracted position to an extended position, for displacing said at least one of said cards placed in said card entrance slot past said snap means when said push plate means is moved from said retracted position to said extended position, thereby placing said at least one of said cards in a stacked condition between said snap means and said pressure plate, said push plate means thereafter returning to said retracted position permitting another of said cards to be placed in said card entrance slot.

2. The stacking disposal system of claim 1, wherein said biasing means comprises a constant force spring, said constant force spring biasing said pressure plate towards said snap means with a force substantially independent of the position of said pressure plate in said magazine between said snap means and said end portion of said magazine.

3. The stacking disposal system of claim 1, wherein said pressure plate moves relative to said magazine along at least one guide rail, and wherein said guide rail is positioned below said magazine.

4. The stacking disposal system of claim 3, wherein said pressure plate comprises a card contact arm, a slide collar and an integral body portion connecting said slide collar with said contact arm, wherein said at least one rail is received by said slide collar.

5. The stacking disposal system of claim 1, wherein said magazine is manually removed from said system, permitting disposal of said cards and replacement of said magazine into said system.

6. The stacking disposal system of claim 1, wherein said push plate means comprises a motor and a push plate moveable by said motor between said retracted and extended positions, said push plate having a card contact surface for contacting said card to push said card past said resilient snap means when said push plate is moved to said extended position.

7. The stacking disposal system of claim 6, wherein said push plate has upper and lower card contact surfaces for contacting upper and lower regions of a card placed in said card slot.

8. The stacking disposal system of claim 1, wherein said snap means comprise a pair of oppositely opposed snaps integral with said first and second sides of said magazine.

9. A stacking disposal system for a plurality of cards having a flat surface and parallel sides, comprising:

a magazine removable from said system having a bottom surface, an end portion and first and second sides extending from said bottom surface;

a card entrance slot for receiving at least one of said cards to be stacked in said magazine;

resilient snaps integral with said first and second sides of said magazine disposed adjacent to said card entrance slot;

a pressure plate moveable within said magazine between said snaps and said end portion of said magazine, said cards being stacked in said magazine between said snaps and said pressure plate, said pressure plate having a card contact surface;

a spring biasing said pressure plate towards said snaps so as to place said card contact surface of said pressure plate in contact with a portion of one of said cards to thereby urge said cards against said snaps;

a push plate reciprocable relative to said card entrance slot from a retracted position to an extended position, a motor for moving said push plate from said retracted position to said extended position for displacing said at least one of said cards placed in said card entrance slot past said snaps when said push plate is moved from said retracted position to said extended position, thereby placing said at least one of said cards in a stacked condition between said snaps and said pressure plate;

said motor thereafter moving said push plate to said retracted position permitting another of said cards to be placed in said card entrance slot.

10. The stacking disposal system of claim 9, wherein said pressure plate moves relative to said magazine along a pair of rails, and where said rails are positioned below said magazine.

11. The stacking disposal system of claim 10, wherein said pressure plate comprises a card contact arm, a slide collar and an integral body portion connecting said slide collar with said contact arm, wherein at least one of said rails is received by said slide collar.

12. The stacking disposal system of claim 10, wherein said system further comprises an optical detector to detect when said magazine is full of said cards.

13. The stacking disposal system of claim 12, wherein said optical detector is mounted adjacent to said end portion of said magazine and responsive to movement of said pressure plate.

14. A stacking disposal system for a sample testing machine for testing a sample contained in a first test sample card, said machine having a test sample card transport system for moving said first test sample card from an incubation station to a reading station, said stacking disposal system comprising:

(a) a magazine for receiving said first test sample card from said test sample card transport system, said magazine having a card entrance slot; and (b) means for stacking said first test sample card in said magazine after said first test sample card has been transported by said test sample card transport system to said card entrance slot in said stacking disposal system, said means for stacking comprising:

(1) a push plate reciprocating in said card entrance slot between retracted and extended positions, said push plate pushing said first test sample card into said magazine when said push plate is in said extended position, and (2) retaining means in said magazine for maintaining said first test sample card pushed into said magazine in a predetermined orientation relative to said magazine and push plate such that, upon introduction of a second test sample card into said card entrance slot, said push plate is operable to push said second test sample card into said magazine into a stacked condition adjacent to said first test sample card.

15. The stacking disposal system of claim 14, wherein said magazine comprises a bottom surface, an end portion and first and second sides extending from said bottom surface.

16. The machine of claim 14, wherein said magazine further comprises a handle permitting a user of the machine to grasp said magazine and remove said magazine from said machine without touching said cards.

17. A stacking disposal system for a sample testing machine for testing a sample contained in a first test sample card, said machine having a test sample card transport system for moving said first test sample card from an incubation station to a reading station, said stacking disposal system comprising:

(a) a magazine for receiving said first test sample card from said test sample card transport system, said magazine having a card entrance slot, a bottom surface, an end portion and first and second sides extending from said bottom surface; and (b) means for stacking said first test sample card in said magazine after said test sample card has been transported by said test sample card transport system to said card entrance slot in said stacking disposal system, said means for stacking comprising:

(1) a push plate reciprocating in said card entrance slot between retracted and extended positions, said push plate pushing said first test sample card into said magazine when said push plate is in said extended position, and (2) retaining means in said magazine for maintaining said first test sample card pushed into said magazine in a predetermined orientation relative to said magazine and push plate such that, upon introduction of a second test sample card into said card entrance slot, said push plate is operable to push said second test sample card into said magazine into a stacked condition adjacent to said first test sample card, (3) said retaining means comprising resilient snap means integral with said first and second sides of said magazine disposed adjacent to said card entrance slot and a pressure plate moveable within said magazine between said snap means and said end portion of said magazine, said pressure plate having a card contact surface; and biasing means for biasing said pressure plate towards said snap means so as to place said pressure plate in contact with a portion of said first test sample card to thereby urge said first test sample card against said snap means;

(4) a motor for moving said push plate from said retracted position to said extended position for displacing said second test sample card placed in said card entrance slot past said snap means when said push plate is moved from said retracted position to said extended position, thereby placing said second test sample card in a stacked condition between said snap means and said pressure plate, said motor thereafter moving said push plate to a retracted position permitting a third test sample card to be placed in said card entrance slot;

wherein said biasing means comprises a constant force spring, said constant force spring biasing said pressure plate towards said snap means with a force substantially independent of the position of said pressure plate in said magazine between said snap means and said end portion of said magazine.

18. The stacking disposal system of claim 17, wherein said pressure plate moves relative to said magazine along at least one guide rail, and wherein said guide rail is positioned below said magazine.

19. The stacking disposal system of claim 11, wherein said slide collar has a length and said card contact arm is positioned at a height H above said slide collar within said magazine, and wherein the ratio of said collar length to H is chosen such that a frictional force between said rail received by said slide collar and said slide collar is less than a force imparted by said push plate onto to said one of said cards placed in said card entrance slot as said card is displaced past said snaps, preventing binding of said pressure plate on said rail.

* * * * *